United States Patent
Yukisada et al.

(10) Patent No.: US 7,643,608 B2
(45) Date of Patent: Jan. 5, 2010

(54) METHOD FOR CHECKING FOR LEAKAGE FROM TUBULAR BATTERIES

(75) Inventors: Hironori Yukisada, Osaka (JP); Takahito Takahashi, Osaka (JP); Masao Nakamura, Osaka (JP); Kazutoshi Okubo, Nara (JP); Masaya Nakata, Osaka (JP)

(73) Assignee: Panasonic Corporation, Osaka (JP)

( * ) Notice: Subject to any disclaimer, the term of this patent is extended or adjusted under 35 U.S.C. 154(b) by 188 days.

(21) Appl. No.: 11/722,930

(22) PCT Filed: Nov. 24, 2005

(86) PCT No.: PCT/JP2005/021537

§ 371 (c)(1),
(2), (4) Date: Jul. 31, 2007

(87) PCT Pub. No.: WO2006/070547

PCT Pub. Date: Jul. 6, 2006

(65) Prior Publication Data

US 2008/0137807 A1   Jun. 12, 2008

(30) Foreign Application Priority Data

Dec. 28, 2004  (JP) .............................. 2004-378454

(51) Int. Cl.
*G01N 23/223* (2006.01)
*G21K 5/08* (2006.01)
(52) U.S. Cl. ........................ 378/44; 378/58; 250/442.11
(58) Field of Classification Search ............. 378/44–50, 378/57, 58; 250/306–308, 440.11, 442.11
See application file for complete search history.

(56) References Cited

U.S. PATENT DOCUMENTS 6,888,917 B2 *   5/2005   Sommer et al. ............... 378/58

(Continued)

FOREIGN PATENT DOCUMENTS

JP    52 138627    11/1977

(Continued)

OTHER PUBLICATIONS

English language Abstract of JP 8-189907.

(Continued)

*Primary Examiner*—Edward J Glick
*Assistant Examiner*—Anastasia Midkiff
(74) *Attorney, Agent, or Firm*—Greenblum & Bernstein P.L.C.

(57) ABSTRACT

In a method for checking for leakage from tubular batteries, when tubular batteries are fed with their respective axial centers aligned in parallel to each other to pass through a leakage check mechanism, a sealed end face of the tubular batteries is irradiated with an X-ray. In accordance with the result of analysis on whether the incident fluorescent X-ray entering a detector contains a fluorescent X-ray associated with an electrolyte component, it is determined whether the tubular batteries have leaked. A length of a detection window of the detector in a direction of feed of the tubular batteries is set to be less than a spacing between the tubular batteries. A length of the detection window oriented orthogonal to the direction of feed is set to be greater than an outer size of the cross-sectional shape of the tubular batteries oriented orthogonal to their axial center.

8 Claims, 5 Drawing Sheets

U.S. PATENT DOCUMENTS

| | | | |
|---|---|---|---|
| 6,888,918 B2 * | 5/2005 | Horai et al. | 378/58 |
| 2005/0153194 A1 | 7/2005 | Kimura et al. | |

FOREIGN PATENT DOCUMENTS

| | | | |
|---|---|---|---|
| JP | 57108744 A * | 7/1982 | |
| JP | 57-148878 | 9/1982 | |
| JP | 57 149942 | 9/1982 | |
| JP | 57149942 A * | 9/1982 | |
| JP | 04284861 A * | 10/1992 | |
| JP | 8 162126 | 6/1996 | |
| JP | 8 189907 | 7/1996 | |
| JP | 9 203714 | 8/1997 | |
| JP | 2001315950 A * | 11/2001 | |
| JP | 2002-246072 | 8/2002 | |
| JP | 2002246072 A * | 8/2002 | |
| JP | 2003 014670 | 1/2003 | |
| JP | 2004-200012 | 7/2004 | |

OTHER PUBLICATIONS

English language Abstract of JP 9-203714.
English language Abstract of JP 8-162126.
English language Abstract of JP 57-149942.
English language Abstract of JP 2003-014670.
Partial English Language Translation of JP 52-138627.
English language Abstract of JP 2004-200012.
English language Abstract of JP 2002-246072.
English language Abstract of JP 57-148878.

* cited by examiner

METHOD FOR CHECKING FOR LEAKAGE FROM TUBULAR BATTERIES

TECHNICAL FIELD

The present invention relates to a method for checking for leakage from tubular batteries in which occurrence of leakage from the sealed end face of a tubular battery is checked by X-ray fluorescence analysis after its manufacture.

BACKGROUND ART

Tubular batteries such as cylindrical or prismatic batteries are sealed, e.g., by inwardly crimping the open end portion of a bottomed tubular battery case to compress an insulating gasket, thereby providing liquid-tight sealing between the battery case, the insulating gasket, and a sealing member. However, even a trace amount of electrolyte deposited on the sealed portion or an imperfect sealing itself would cause the interface between two components in the sealing structure to be wetted with the electrolyte. This may lead to the development of a leakage path, resulting in leakage occurring by the electrolyte migrating along the leakage path. In particular, in those batteries with an alkaline electrolyte, the alkaline electrolyte itself migrates along the surface of the negatively charged metallic sealing member or battery case. Leakage is thus more likely to happen in these batteries when compared with other types of batteries.

Conventionally, to check for the occurrence of leakage, a given number of tubular batteries were arranged side by side with their sealed end faces oriented upwardly. The sealed end face of each tubular battery was then covered with a cloth, to which a reagent was then applied. While the cloth was being tapped with a brush, the tubular battery whose yellow reagent discolored purple was visually identified and determined to be leaky. However, such inspection means that relies on operators' manual operations and visual determinations is limited in terms of the handling speed and thus very inefficient. The inspection is also likely to be inaccurate because variations exist among individual operators and they may overlook leakage. To be worse, such a leakage that occurs immediately inside the sealed end face cannot be visually identified.

In this context, such inspection means has been recently adopted which allows for determining occurrence of leakage by X-ray fluorescence analysis. According to a first one of those conventional techniques, a primary X-ray having a certain pre-defined wavelength is used to irradiate a tubular battery, and a fluorescent X-ray coming out of the tubular battery is allowed to be incident upon an analyzer. The analyzer analyzes whether the incident fluorescent X-ray contains such a fluorescent X-ray that has a wavelength associated with an electrolyte component. Then, based on the output from the analyzer, occurrence of leakage is determined (for example, see Patent Document 1).

On the other hand, according to a second conventional technique, while tubular batteries are being fed in a row at predetermined intervals, each tubular battery is irradiated with an X-ray from an X-ray source. Those fluorescent X-rays arising from the sealed end face and a side of a tubular battery are allowed to be incident upon a plurality of detectors located around the X-ray source. Based on the results of detections provided by the plurality of detectors, a tubular battery with the electrolyte deposited thereon is identified (for example, see Patent Document 2).

[Patent Document 1] Japanese Patent Laid-Open Publication No. Sho 52-138627
[Patent Document 2] Japanese Patent Laid-open Publication No. Hei 9-203714

DISCLOSURE OF THE INVENTION

Problems to be Solved by the Invention

However, any of the aforementioned conventional techniques cannot check tubular batteries at high speeds with accuracy. That is, the first conventional technique cannot increase the speed of inspection because batteries are checked one by one with a battery placed opposite to the X-ray source. On the other hand, in the second conventional technique, four detectors placed in a rectangular arrangement are used also to detect the electrolyte deposited on a side of the tubular batteries, thereby requiring the batteries to be arranged at relatively large intervals. This arrangement places a limitation on the speed of inspection as well as causes an increase in the size of the system and costs.

Furthermore, in the inspection of leakage from a battery that employs an alkaline electrolyte, it is commonly practiced to analyze the intensity of a fluorescent X-ray emitted from the potassium in the alkaline electrolyte. However, with the first and second conventional techniques, the fluorescent X-ray is incident upon the detector through a path in which air is present. This raises a problem that an element that is contained in the air, especially argon, emits a fluorescent X-ray of a wavelength similar to that of potassium, thereby exerting an adverse effect on the detection of the intensity of the potassium to degrade the accuracy of detection.

The present invention was developed in light of the aforementioned conventional problems. It is therefore an object of the present invention to provide a method for checking for leakage from tubular batteries, in which occurrence of leakage from tubular batteries is determined at high speeds with accuracy by X-ray fluorescence analysis.

Means for Solving the Problems

To achieve the aforementioned object, a method for checking for leakage from tubular batteries according to the present invention includes: feeding tubular batteries with respective axial centers thereof aligned in parallel to each other to pass through a leakage check section placed opposite to a detection window of a leakage check mechanism; irradiating a sealed end face of the tubular battery in the leakage check section with an X-ray through the detection window and allowing a fluorescent X-ray coming out of the sealed end face to enter a fluorescent X-ray detector through the detection window; and analyzing whether a fluorescent X-ray associated with an electrolyte component is contained in the incident fluorescent X-ray to thereby determine whether leakage occurs from the tubular battery. In the method, the detection window is defined in such a shape that a length thereof in a direction of feed of the tubular batteries is less than a spacing between the tubular batteries being fed, and a length thereof in an orientation orthogonal to the direction of feed is slightly larger than an outer size of the cross-sectional shape of the tubular batteries in an orientation orthogonal to their axial center.

In such an arrangement, when the tubular batteries with their respective axial centers aligned in parallel to each other pass through the leakage check section opposite to the detection window of the leakage check mechanism, a fluorescent X-ray emitted from the sealed end face of the tubular batteries irradiated with the primary X-ray enters the fluorescent X-ray detector through the detection window. Since the detection window is defined in such a shape that its length in the direction of feed of the tubular batteries is less than the spacing between the tubular batteries, the fluorescent X-ray coming out of each of two adjacent tubular batteries will never simultaneously enter the fluorescent X-ray detector through the detection window. Accordingly, even when the tubular batteries arranged at the smallest possible spacing are each fed at a high speed, it is ensured that the fluorescent X-rays emitted from individual tubular batteries and incident upon the fluorescent X-ray detector are separately identified, thereby allowing for dramatically increasing the speed of checking for leakage.

On the other hand, the length of the detection window in an orientation orthogonal to the direction of feed is defined to be slightly greater than the outer size of the cross-sectional shape of the tubular batteries in an orientation orthogonal to their axial center. This ensures that the fluorescent X-ray emitted from any part of the sealed end face of the tubular batteries enters the fluorescent X-ray detector, thereby making it possible to detect occurrence of leakage wherever the leakage has occurred on the sealed end face. It is also possible to detect a predetermined fluorescent X-ray incident upon the fluorescent X-ray detector with high accuracy at a high S/N ratio. Furthermore, since the X-ray and fluorescent X-ray pass through the insulating gasket or the like, it is possible to positively detect even such a leakage occurring inside the tubular batteries that could not be visually determined.

Furthermore, occurrence of leakage may be detected in accordance with an intensity per unit time of the fluorescent X-ray successively entering the fluorescent X-ray detector from each tubular battery which sequentially comes to oppose the detection window while being fed, or in accordance with an intensity per unit area of the sealed end face of the tubular battery. This makes it possible to highly accurately detect occurrence of leakage from the tubular batteries being fed even at high speeds no matter how each of the tubular batteries arranged in position is fed, i.e., continuously at a constant speed, intermittently at a standstill in the leakage check section where the tubular battery opposes the detection window, or variably at a low speed only when the tubular battery passes through the leakage check section. This is because occurrence of leakage is determined in accordance with either one of the following intensities. That is, the intensities include the strength or a fluorescent X-ray per unit time that is determined by dividing the fluorescent X-ray incident from a tubular battery when passing through the leakage check section by the time required for the entire tubular battery to completely pass by the detection window. The intensities also include the strength of a fluorescent X-ray per unit area that is determined by dividing the fluorescent X-ray incident from a tubular battery when passing through the leakage check section by the surface area of the sealed end face of the tubular battery.

Furthermore, the detection window of the leakage check mechanism may be disposed to oppose the sealed end face of the tubular battery being fed at a predetermined distance therebetween. The housing of the check mechanism may contain an X-ray source for emitting an X-ray to a tubular battery, a mask for condensing a fluorescent X-ray emitted from the X-ray source into a beam, and the fluorescent X-ray detector upon which the fluorescent X-ray is incident. Additionally, the inside of the housing may be kept in a helium gas atmosphere, thereby allowing the helium gas filled in the housing to reduce the argon gas contained in the air. It is thus possible to remove adverse effects exerted by the argon gas on the fluorescent X-ray, thereby eliminating noise caused by the argon gas and highly accurately detecting the strength of the fluorescent X-ray at a high S/N ratio. However, in this case, to prevent leakage of the helium gas out of the detection window, it is preferable to close the detection window with a sealing member made of a material that transmits the X-ray. Furthermore, since the mask can condense the primary X-ray into a beam, the opening area of the detection window can be reduced as small as possible. Additionally, the distance between the detection window and the sealed end face of the tubular batteries being fed through the leakage check section can be set, for example, to be as small as approximately 2 mm. It is thus possible to reduce the adverse effects caused by an argon gas contained in the air that is present between the detection window and the sealed end face of the tubular batteries, thereby improving the accuracy of detecting leakage.

Furthermore, the tubular batteries may be fed while being held on transfer disks in parallel to each other at regular intervals. This allows each of the tubular batteries arranged and held on the transfer disks in the predetermined manner to be fed in a rotary scheme toward the leakage check section. Accordingly, unlike a case where the tubular batteries disposed upright are fed on a conveyor, there is no possibility of the tubular batteries toppling over, and thus the speed of feed can be significantly increased. Furthermore, even when the tubular batteries are each fed at high speeds, the transfer disks positively hold the tubular batteries so that they are not displaced out of position while being fed at the high speeds. This ensures that the sealed end face of the tubular batteries can pass by the detection window at the shortest possible constant distance therebetween. It is thus possible to detect leakage from the tubular batteries with high accuracy while they are beings fed at high speeds.

Furthermore, the housing which accommodates the X-ray source, the mask, and the fluorescent X-ray detector may be installed in front of an apparatus casing, to which the transfer disks for feeding the tubular batteries are attached, so that the detection window provided on the housing opposes the transfer disks. In this arrangement, the housing is attached to the support mount so that the detection window which transmits the primary X-ray is oriented backwardly in consideration of the operator normally working only in front of the support mount opposite to the attachment of the transfer disks. This arrangement allows for eliminating the risk of the operator being exposed to the primary X-ray, thereby embodying a very safe leakage check system in practically realizing a leakage check method of the present invention.

Furthermore, each of the tubular batteries may be held in position on the transfer disks to pass through the leakage check mechanism so that a defective tubular battery which is determined to be leaky as a result of a check in the leakage check mechanism is rejected from the transfer disks onto a detectives collection path in order to be separated from a good-battery feed path. This arrangement allows for automatically ejecting, out of the feed path, those defective tubular batteries that have been determined to be leaky in the process of continual checks for leakage, thereby eliminating the need for providing a screening step that is carried out in accordance with the results of inspections of tubular batteries after the leakage check process.

Furthermore, an alkaline battery made up of an electrolyte containing a potassium hydroxide solution may be checked to determine occurrence of leakage based on whether a fluorescent X-ray associated with a potassium component is contained in the fluorescent X-ray incident upon the fluorescent X-ray detector. Here, the potassium that is apt to emit a fluorescent X-ray is defined as the object to be checked. Thus, when applied to the detection of leakage from a battery employing an alkaline electrolyte, this arrangement allows for relying on the strength of a component associated with the potassium contained in the fluorescent X-ray to detect occurrence of leakage with high detection accuracy.

Furthermore, the mask formed of a metal that does not transmit an X-ray may be allowed to condense an X-ray emitted from the X-ray source into a beam, and the beam may be then transmitted through the detection window on the housing to the sealed end face of the tubular batteries being fed. At least a length of the detection window in the direction of feed of the tubular batteries may be made variable, thereby allowing the size of the opening of the detection window to be variably adjusted corresponding to the diameter or the outer shape of a tubular battery to be checked. This makes it possible to readily perform a leakage inspection on various types of tubular batteries such as cylindrical batteries having different diameters or prismatic batteries having different outer shapes.

BEST MODE FOR CARRYING OUT THE INVENTION

Figure 7A:
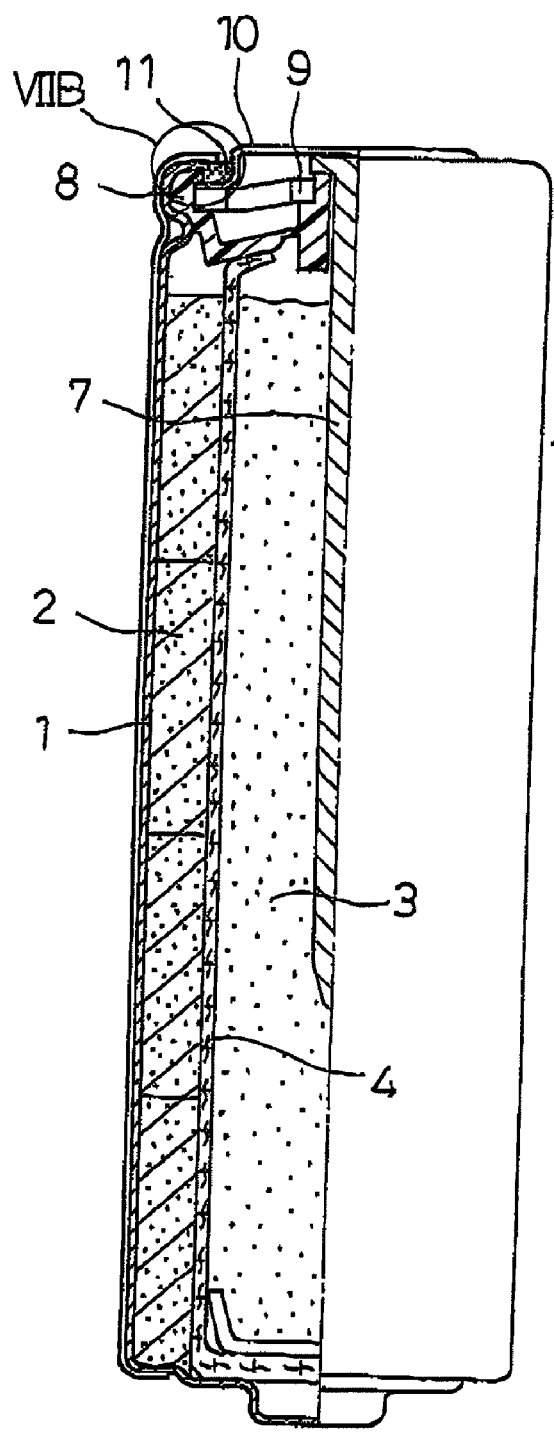
FIG. 7A is a partially cut away front view illustrating an example of a battery which employs an alkaline electrolyte and is checked by a leakage check method of the present invention, FIG. 7B being an enlarged view of portion "VIIB" of FIG. 7A.

Now, a method for checking for leakage from tubular batteries according to the present invention will be described in more detail in accordance with the embodiments with reference to the drawings. To begin with, a tubular battery will be described which is checked by a leakage check method of the present invention. FIG. 7A is a partially cut away front view illustrating an example of a tubular battery Ba to be checked that employs an alkaline electrolyte. The tubular battery Ba is configured such that a mixed positive electrode 2 and a gel zinc negative electrode 3, separated from each other by the intervention of a separator 4, are housed in a bottomed cylindrical metallic battery case 1 in conjunction with an electrolyte (not shown). Additionally, the tip of an electron collector 7 inserted in the gel zinc negative electrode 3 is disposed at the opening portion of the battery case 1, and the opening portion of the battery case 1 is sealed with an insulating gasket 8, a washer 9, and a negative electrode terminal plate 10.

The opening portion of the battery case 1 of the aforementioned tubular battery Ba is sealed as follows. That is, the opening rim portion of the battery case 1 is crimped inwardly with the mutually overlapped peripheral edge portion of each of the washer 9 and the negative electrode terminal plate 10 being sandwiched by the insulating gasket 8. This causes the insulating gasket 8 to be compressively deformed, thereby providing hermeticity between the battery case 1, the insulating gasket 8, the negative electrode terminal plate 10, and the washer 9. With the tubular battery Ba, there is a possibility that the electrolyte may slightly leak through the interface between the opening rim portion of the battery case 1 and the insulating gasket 8 or between the negative electrode terminal plate 10 and the insulating gasket 8.

Figure 7B:
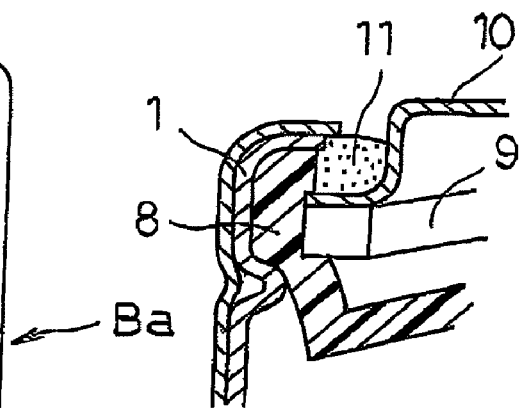

Additionally, as shown in FIG. 7B or an enlarged view of portion VIIB of FIG. 7A, an insulating resin 11 is applied as illustrated between the peripheral opening end of the battery case 1, the end face of the insulating gasket 8, and the negative electrode terminal plate 10. Alternatively, instead of the insulating resin 11, an insulating ring may also be fitted therein. However, in any of these cases, it is intended to prevent electric short circuits between the opening rim portion of the battery case 1 and the negative electrode terminal plate 10. Note that the insulating gasket 8 may also be disposed to allow its end face to protrude from the opening rim portion of the battery case 1.

However, for example, in the manufacturing process of the tubular battery Ba, a trace amount of electrolyte may be deposited on any one of the negative electrode terminal plate 10t the insulating gasket 8, or the battery case 1. Even the trace amount of electrode causes the interface between two of the members, on which the electrolyte is deposited, to be wetted with the electrolyte. This may result in a leakage path being developed therebetween, causing the electrolyte to leak along the leakage path. Such a leakage cannot be visually identified from outside due to the intervention of the aforementioned insulating resin 11 or the like. The leakage check method of the present invention is intended to ensure, by X-ray fluorescence analysis, the detection of occurrence of such leakage that cannot be visually identified.

Figure 1:
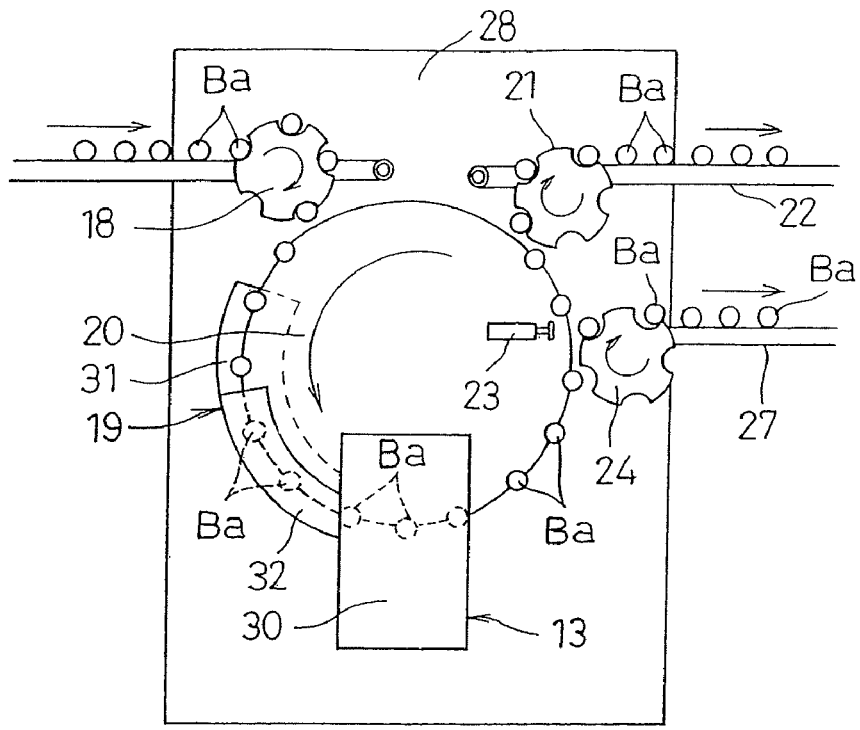
FIG. 1 is a schematic front view illustrating a leakage check system according to an embodiment which embodies a method for checking for leakage from tubular batteries in accordance with the present invention.
Figure 2:
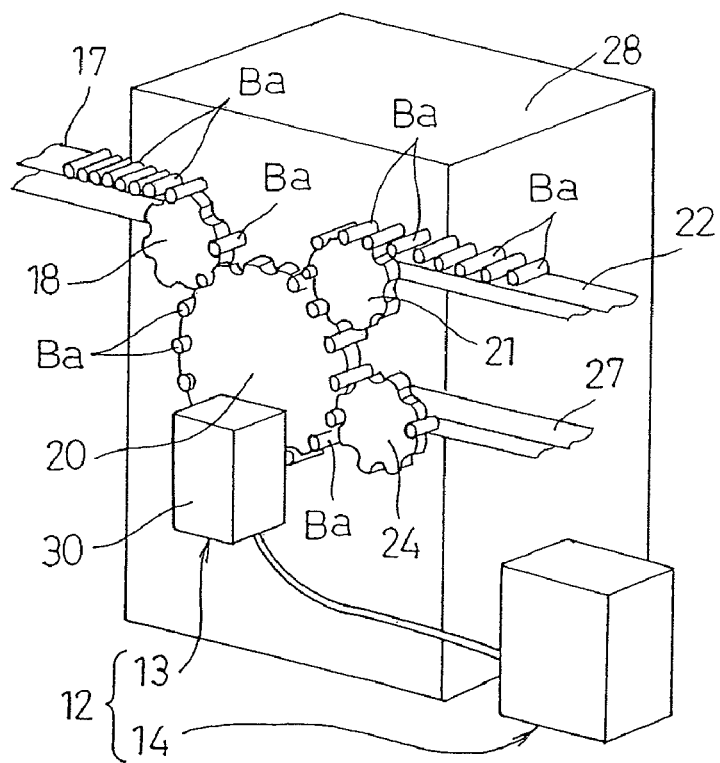
FIG. 2 is a schematic perspective view illustrating the aforementioned leakage check system.

FIGS. 1 and 2 are a schematic front view and a schematic perspective view illustrating a leakage check system which embodies a method for checking for leakage from tubular batteries according to the present invention. As shown in FIG. 2, the leakage check system has a leakage check mechanism 12 for determining by X-ray fluorescence analysis whether leakage has occurred from the tubular battery Ba. The leakage check mechanism 12 includes a fluorescent X-ray detection portion 13 and an analysis portion 14. The tubular batteries Ba or an object to be checked are fed on a supply conveyor 17. When transferred from the supply conveyor 17 to a supply transfer disk 18, the tubular batteries Ba are held on the supply transfer disk 18 with their respective axial centers arranged to be parallel to each other at regular intervals.

Furthermore, when the tubular batteries Ba are transferred from the supply transfer disk 18 to a main transfer disk 20 to pass through an alignment mechanism 19 of FIG. 1, the position in the orientation of their respective axial centers is realigned so that their sealed end faces are flush with each other for passage through the leakage check mechanism 12. Then, those tubular batteries Ba that have successfully passed the check at the leakage check mechanism 12 are transferred to an unloading transfer disk 21 and then fed on an unloading conveyor 22 to the next process. On the other hand, those tubular batteries Ba that have failed the aforementioned check are pushed out of the main transfer disk 20 by an ejection cylinder 23 being driven when the tubular batteries Ba are fed to a defectives ejection position as the main transfer disk 20 rotates, and thereby transferred to an ejection transfer disk 24. Thereafter, the tubular batteries Ba are conveyed on an ejection conveyor 27 to be ejected to a defectives bin or the like.

Furthermore, each of the transfer disks 18, 20, 21, and 24 is designed to hold the tubular batteries Ba, which are fitted in the retaining grooves, by magnetic holding means, chucking means, or vacuuming means so that the tubular batteries Ba are not easily displaced. Accordingly, unlike a case where the tubular batteries Ba disposed upright are fed on a conveyor, there is no possibility of the tubular batteries Ba toppling over or dropping off, and thus the speed of feed can be significantly increased. Since each of the transfer disks 18, 20, 21, and 24 is disposed to rotate in a vertical plane, it is also possible to reduce the footprint of the system, thereby providing a high degree of flexibility in installation.

Figure 3:
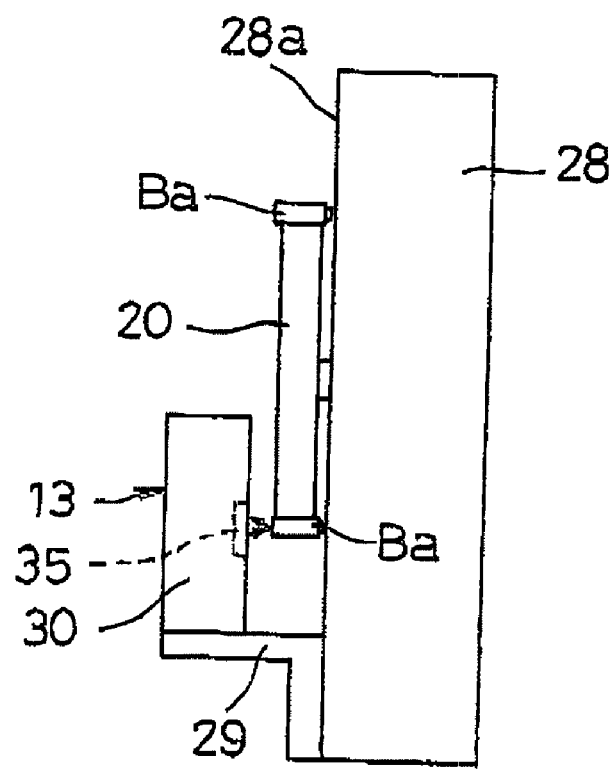
FIG. 3 is a schematic right-side view illustrating the aforementioned leakage check system.

FIG. 3 is a schematic right-side view illustrating the aforementioned leakage check system. In the figure, an apparatus casing 28 of the leakage check system is provided, on its front 28a, with each of the transfer disks 18, 20, 21, and 24 mentioned above, and the drive mechanism and the drive control mechanism for each of these transfer disks 18, 20, 21, and 24 are installed inside the apparatus casing 28. A support mount 29 is securely fixed to a lower portion on the front 28a of the apparatus casing 28. A housing 30 of the aforementioned fluorescent X-ray detection portion 13 is installed on top of the support mount 29 so that a detection window 35 provided on the housing 30 is aligned opposite to the main transfer disk 20 on the front 28a of the apparatus casing 28.

Figure 4:
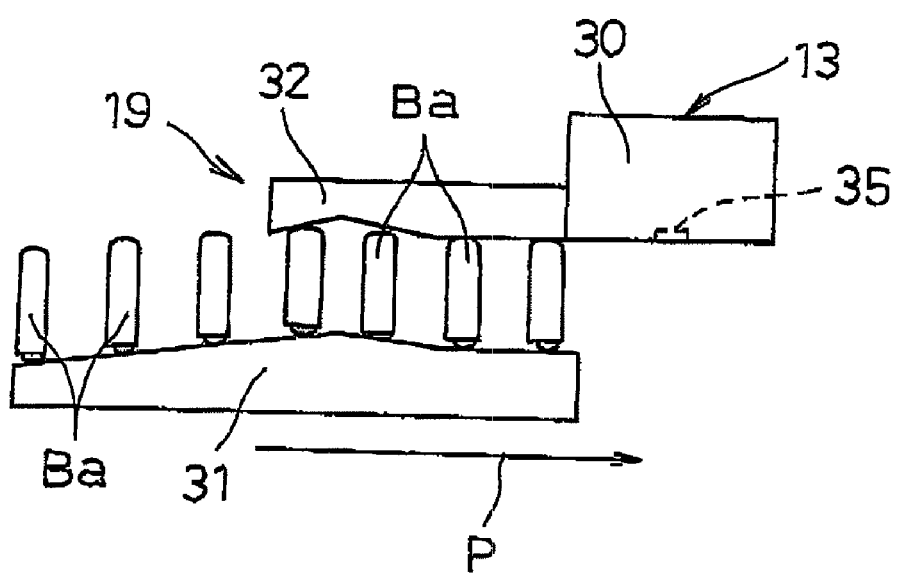
FIG. 4 is a schematic plan view illustrating an alignment mechanism for a tubular battery in the aforementioned leakage check system.

Furthermore, as shown in FIG. 4, the alignment mechanism 19 shown in FIG. 1 includes a follower guide body 31 which causes each of the tubular batteries Ba, which are held at regular intervals on the main transfer disk 20 and fed in a direction of feed P, to be guided and sequentially aligned with the fluorescent X-ray detection portion 13. The alignment mechanism 19 further includes an alignment guide body 32 for abutting and thereby aligning the sealed end faces (the upper end faces in the figure) of the tubular batteries Ba, which are being fed with their orientation slightly changed by the follower guide body 31, so that the sealed end faces are flush with each other. With this arrangement, each of the tubular batteries Ba, which are held on the main transfer disk 20 with their respective sealed end faces aligned to be flush with each other, is fed at a predetermined fixed distance from the detection window 35 on the housing 30 of the fluorescent X-ray detection portion 13.

Figure 5:
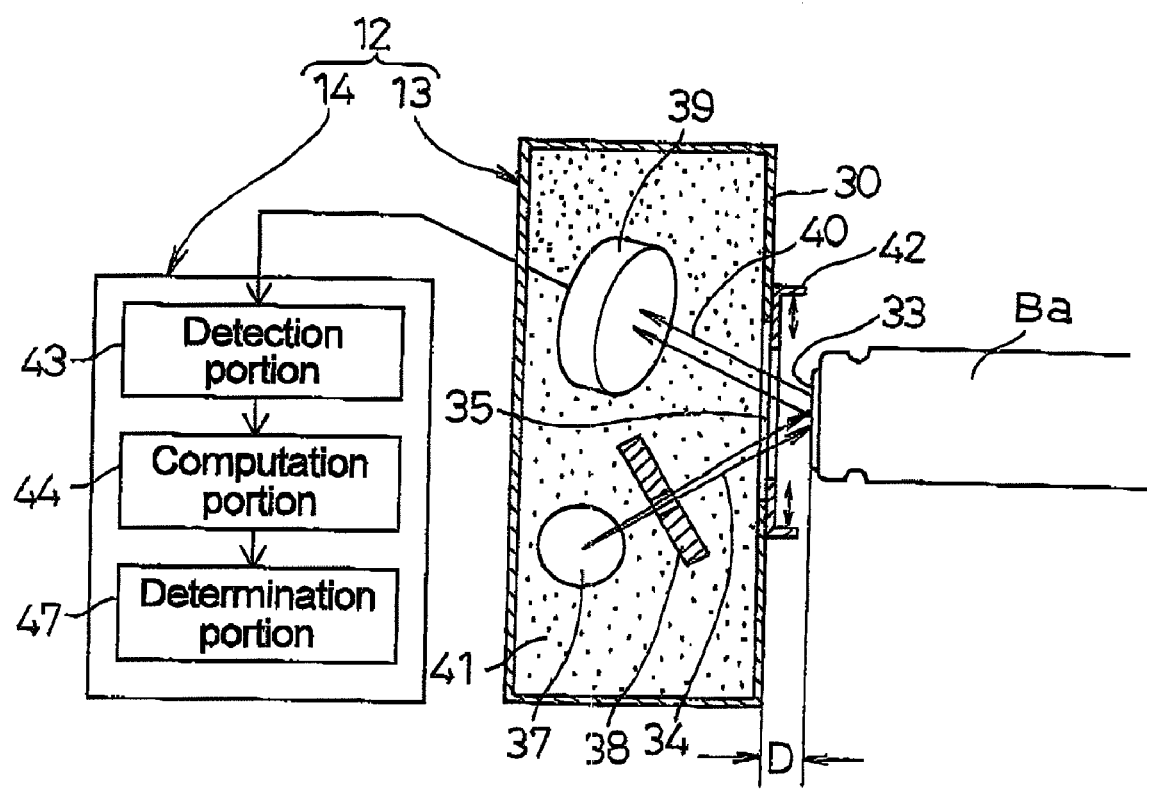
FIG. 5 is a schematic view illustrating the configuration of a leakage check mechanism in the aforementioned leakage check system.

FIG. 5 is a schematic view illustrating the configuration of the aforementioned leakage check mechanism 12. As also shown in FIG. 2, the leakage check mechanism 12 includes the fluorescent X-ray detection portion 13 and the analysis portion 14. In the housing 30, the fluorescent X-ray detection portion 13 includes an X-ray tube 37 serving as an X-ray source for irradiating the sealed end face 33 of the tubular batteries Ba with a primary X-ray 34 while the tubular batteries Ba are being securely carried on the aforementioned main transfer disk 20. Also included are a mask 38 for transmitting the primary X-ray 34 as a condensed beam through the detection window 35 on the housing 30, and a fluorescent X-ray detector 39 for receiving, through the detection window 35, the fluorescent X-ray (secondary X-ray) 40 that is emitted from the sealed end face 33 of the tubular batteries Ba when irradiated with the primary X-ray 34. The aforementioned mask 38 is formed of a metal such as brass that does not transmit the X-ray 34. Furthermore, the inside of the housing 30 is kept in an atmosphere of a helium gas 41, and the detection window 35 is accordingly sealed with a sealing member (not shown) made of a material such as PET film that transmits the X-rays 34 and 40. Furthermore, the housing 30 is provided with an opening control member 42, which does not transmit X-ray, for varying the shape of the opening of the detection window 35 as desired.

On the other hand, the analysis portion 14 includes a detection portion 43, a computation portion 44, and a determination portion 47. The detection portion 43 detects only such a fluorescent X-ray 40 that has a wavelength associated with a predetermined component (element) among the fluorescent X-rays 40 incident upon the fluorescent X-ray detector 39. The computation portion 44 divides the fluorescent X-ray 40 detected at the detection portion 43 by the time required for a single tubular battery Ba to completely pass by its opposite area on the detection window 35, thereby determining the strength of the fluorescent X-ray 40 per unit time. The determination portion 47 compares the strength determined by the computation portion 44 with a pre-set level to determine whether leakage occurs from the tubular battery Ba.

An element or one of the components of the electrolyte is pre-defined which is not used in any other parts of the tubular battery Ba and which emits an intense fluorescent X-ray. The aforementioned detection portion 43 detects the fluorescent X-ray 40 that the element emits at its wavelength. For example, suppose that an object to be checked is a tubular battery Ba that employs an alkaline electrolyte. In this case, the detection portion 43 detects the potassium in the electrolyte of a potassium hydroxide solution.

Instead of computing the aforementioned strength of the fluorescent X-ray 40 per unit time, the aforementioned computation portion 44 may also divide the fluorescent X-ray 40 detected at the detection portion 43 by the surface area of the sealed end face 33 of a single tubular battery Ba to determine the strength of the fluorescent X-ray 40 per unit area.

The aforementioned determination portion 47 is adapted to determine that leakage has occurred when the strength of the fluorescent X-ray 40 per unit time or the strength of the fluorescent X-ray 40 per unit area computed by the computation portion 44 is above a quantitative analysis value. The quantitative analysis value, which is experimentally pre-determined and stored as a setting, is indicative of the minimum quantity above which occurrence of leakage can be determined by a conventional manual visual inspection.

Figure 6A:
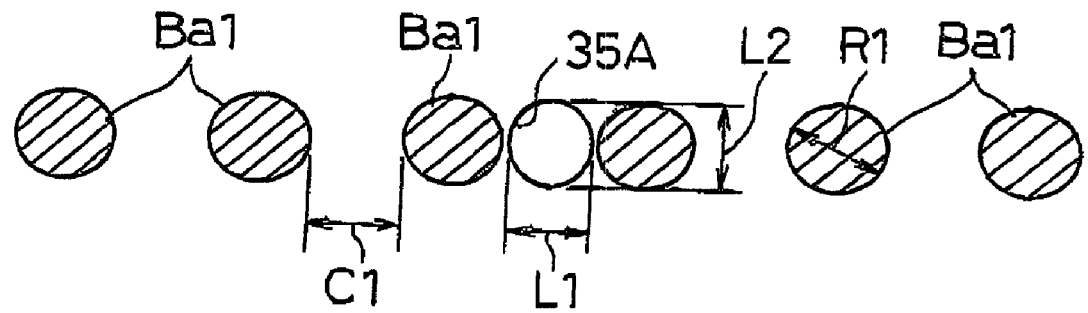
FIGS. 6A to 6C are explanatory views illustrating the relative relationship between the arrangement of detection windows having different shapes and respective tubular batteries and the shape of their sealed end face in the aforementioned leakage check mechanism.
Figure 6B:
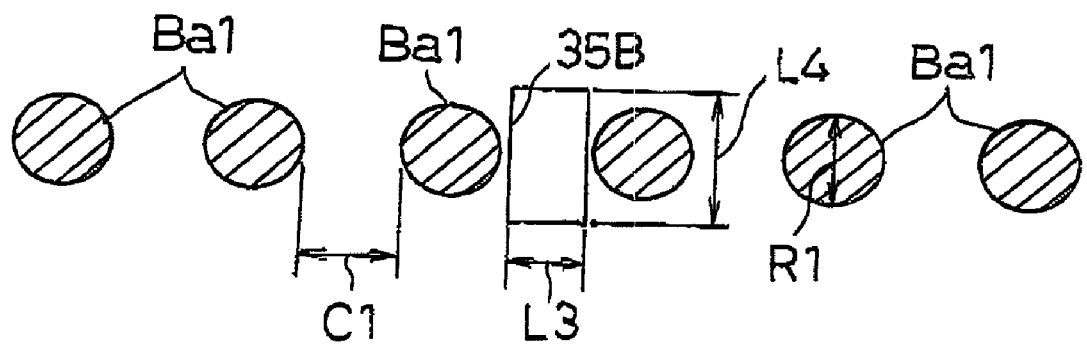
Figure 6C:
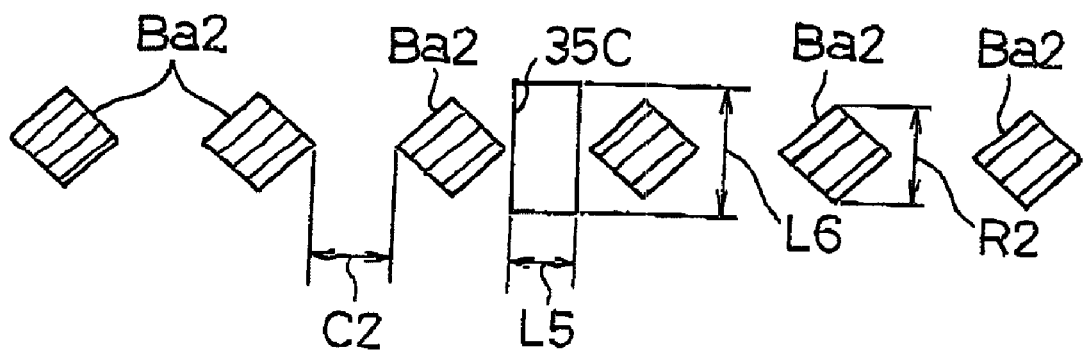

FIGS. 6A to 6C are explanatory views illustrating the relative relationship between the arrangement of detection windows 35A to 35C having different shapes and respective tubular batteries Ba1 and Ba2 and the shape of a sealed end face 33 in the fluorescent X-ray check apparatus 13. FIG. 6A shows the detection window 35A having a circular opening for a cylindrical battery Ba1. FIG. 6B shows the detection window 35B having a rectangular opening for the cylindrical battery Ba1. FIG. 6C shows the detection window 35C having a rectangular opening for the prismatic battery Ba2.

The detection window 35A shown in FIG. 6A for the cylindrical batteries Ba1 is formed in the shape of a circular opening such that its length in a direction of feed (here, its diameter since it is circular) L1 is less than a spacing C1 between the cylindrical batteries Ba1 being fed. In addition to this, its length in an orientation orthogonal to the direction of feed (here, also its diameter) L2 is greater than an outer size R1 of the cross-sectional shape of the cylindrical batteries Ba1 in an orientation orthogonal to their axial center (here, their diameter since they are circular).

The detection window 358 shown in FIG. 6B for the cylindrical batteries Ba1 is formed in the shape of a rectangular opening such that its length L3 in the direction of feed is less than the spacing C1 between the cylindrical batteries Ba1 being fed. In addition to this, its length L4 in an orientation orthogonal to the direction of feed is greater than the outer size R1 of the cross-sectional shape of the cylindrical batteries Ba1 in an orientation orthogonal to their axial center.

The detection window 35C shown in FIG. 6C for the prismatic batteries Ba2 is formed in the shape of a rectangular opening such that its length L5 in the direction of feed is less than a spacing C2 between the prismatic batteries Ba2 being fed. In addition to this, its length L6 in an orientation orthogonal to the direction of feed is greater than an outer size R2 of the cross-sectional shape of the prismatic batteries Ba2 in an orientation orthogonal to their axial center.

A description will now be made to the inspection process in the aforementioned leakage check system that embodies a leakage check method of the present invention. As shown in FIGS. 1 and 2, the tubular batteries Ba having been fabricated to serve as a battery are transferred to the main transfer disk 20 via the supply conveyor 17 and the supply transfer disk 18, to be thereby aligned and held in parallel to each other at predetermined intervals on the main transfer disk 20. Then, in a step where they are fed to the leakage check mechanism 12 as the main transfer disk 20 rotates, the alignment mechanism 19 aligns their positions in the orientation of their axial center so that their respective sealed end faces 33 are flush with each other, and thereafter they are kept as aligned. Therefore, as shown in FIG. 5, each of the tubular batteries Ba is allowed to pass through the leakage check mechanism 12 while each sealed end face 33 is always kept at a fixed constant distance D to the detection window 35. Accordingly, the distance D from the sealed end face 33 to the detection window 35 can be set to a very small value, for example, approximately 2 mm.

When each of the tubular batteries Ba passes through the leakage check section that opposes the detection window 35, the primary X-ray 34 emitted from the X-ray tube 37 is condensed through the mask 38 into a beam, which passes through the detection window 35 to irradiate the sealed end face 33 of a tubular battery. Then, the fluorescent X-ray 40 coming out of the sealed end face 33 enters the fluorescent X-ray detector 39 through the detection window 35. In the analysis portion 14, among the fluorescent X-rays 40 that are incident upon and detected by the fluorescent X-ray detector 39, the detection portion 43 detects only such a fluorescent X-ray 40 that has a wavelength associated with a predefined one of those components contained in the electrolyte. As the predefined component, it is preferable to define an element of the components of the electrolyte which is not used in any other parts of the tubular batteries Ba and emits an intense fluorescent X-ray 40. For example, when an object to be checked is a tubular battery Ba that employs an alkaline electrolyte, it is preferable to define potassium in the electrolyte of a potassium hydroxide solution.

The computation portion 44 of the analysis portion 14 has the following various types of data pre-stored therein. That is, the computation portion 44 has at least the following time settings stored therein. These settings include: the timing at which the end portion of each of the tubular batteries Ba in the direction of feed is brought to oppose the detection window 35; the time required for a tubular battery Ba to completely pass by the detection window 35 when the main transfer disk 20 is continuously driven at a constant rotational speed and driven at a varied low speed when the tubular battery Ba is passing by the detection window 35 opposing thereto; the standstill time during which the main transfer disk 20 is intermittently driven to allow a tubular battery Ba to temporarily stand still opposing the detection window 35; and the surface area of the sealed end face 33 of various types of tubular batteries Ba to be checked.

Furthermore, the aforementioned computation portion 44 divides the fluorescent X-ray 40, which is detected at the detection portion 43 from the predefined timing point until any one of the aforementioned time, settings has elapsed, by the time required for a single tubular battery Ba to completely pass by the detection window 35. In this manner, the strength of the fluorescent X-ray 40 per unit time is determined. Alternatively, the aforementioned computation portion 44 divides the fluorescent X-ray 40, which is detected at the detection portion 43 from the predefined timing point until any one of the aforementioned time settings has elapsed, by the surface area of the sealed end face 33 of a tubular battery Ba being inspected. In this manner, the strength of the fluorescent X-ray 40 per unit area is determined. Subsequently, the determination portion 47 compares the strength determined by the computation portion 44 with the predefined level which has been experimentally determined through a manual visual inspection as described above. Then, when the determined strength is above the level setting, the determination portion 47 determines that leakage has occurred in the tubular battery Ba.

As explained in relation to FIGS. 6A to 6C, in determining occurrence of leakage by X-ray fluorescence analysis as described above, any one of the circular detection window 35A or the rectangular detection windows 35B and 35C may be employed as the detection window 35. In any case, the length L1, L3, and L5 of the detection windows 35A to 35C in the direction of feed of the tubular batteries Ba1 and Ba2 are defined to be less than the spacing C1 or C2 between the tubular batteries Ba1 or Ba2. Accordingly, even when each of the tubular batteries Ba1 and Ba2 arranged at the smallest possible spacing C1 or C2 is fed at high speeds, the fluorescent X-rays 40 from two adjacent ones of the respective tubular batteries Ba1 and Ba2 will never simultaneously enter the fluorescent X-ray detector 39 through the detection window 35B or 35C. Accordingly, the fluorescent X-rays 40 emitted individually from the tubular batteries Ba1 and Ba2 and received by the fluorescent X-ray detector 39 can be separately identified, thereby allowing for dramatically increasing the speed of checking for leakage. As a result of actual measurements, it was ensured that 800 to 1200 tubular batteries Ba were checked per one minute, and the inspection speed can be further increased to such an extent as to check 2000 tubular batteries Ba per one minute.

Furthermore, the lengths L2, L4, and L6 of the detection windows 35A to 35C in an orientation orthogonal to the direction of feed are defined to be slightly greater than the outer sizes R1 and R2 of the cross-sectional shape of the tubular batteries Ba1 and Ba2 in an orientation orthogonal to their axial center. This ensures that the fluorescent X-ray 40 emitted from any part of the sealed end face 33 of the tubular batteries Ba1 and Ba2 enters the fluorescent X-ray detector 39, thereby allowing for detecting occurrence of leakage even when the leakage occurs at any part of the sealed end face 33. Furthermore, the aforementioned lengths L2, L4, and L6 are defined to be slightly larger than the outer sizes R1 and R2 of the aforementioned cross-sectional shapes, thereby allowing the detection windows 35A to 35C to block the entry of a fluorescent X-ray from the surrounding of the tubular batteries Ba1 and Ba2 into the fluorescent X-ray detector 39. It is thus possible for the detection portion 43 of the analysis portion 14 to detect, at a good S/N ratio, the fluorescent X-ray 40 having a predetermined wavelength among the fluorescent X-rays 40 that are incident upon the fluorescent X-ray detector 39.

Furthermore, the computation portion 44 and the determination portion 47 of the analysis portion 14 determine occurrence of leakage by comparing either one of the following intensities with a level setting that is experimentally predetermined. That is, the intensities include the strength of the fluorescent X-ray 40 per unit time that is determined by dividing the fluorescent X-ray 40 of the predetermined wavelength, which has entered the fluorescent X-ray detector 39 when a tubular battery Ba passes by the detection window 35, by the time required for the entire tubular battery Ba to completely pass by the detection window 35. The intensities also include the strength of the fluorescent X-ray 40 per unit area that is determined by dividing the fluorescent X-ray of the predetermined wavelength, which has entered the fluorescent X-ray detector 39 when the entire tubular battery Ba passes by the detection window 35, by a cross-sectional area corresponding to the surface area of the sealed end face 33 of the tubular battery Ba. This makes it possible to highly accurately detect occurrence of leakage no matter how the tubular batteries Ba are fed, for example, continuously at a constant speed, intermittently at a standstill when a tubular battery Ba opposes the detection window 35, or variably at a low speed when a tubular battery Ba passes by the detection window 35.

Furthermore, the inside of the housing 30 of the fluorescent X-ray detection portion 13 is kept in an atmosphere of the helium gas 41, and the helium gas 41 reduces the argon gas contained in the air. It is thus possible to remove adverse effects exerted by the argon gas that emits a fluorescent X-ray 40 at a wavelength that is similar to that of the potassium to be detected. This allows for eliminating noise caused by the argon gas and thereby highly accurately detecting the strength of the fluorescent X-ray 40 of the predetermined wavelength at a high S/N ratio.

In the aforementioned fluorescent X-ray detection portion 13, the mask 38 condenses the primary X-ray 34 into a beam, thereby allowing the opening area of the detection windows 35A to 35C to be reduced as small as possible as explained in relation to FIGS. 6A to 6C. In addition to this, the distance D (see FIG. 5) between the detection window 35A to 35C and the sealed end face 33 of the tubular batteries Ba1 and Ba2 being fed can be set to as small a value as approximately 2 mm as described above. It is thus possible to dramatically reduce the aforementioned adverse effects caused by an argon gas contained in the air that is present between the detection window 35A to 35C and the sealed end face 33 of the tubular batteries Ba1 and Ba2 being fed. This also allows for further improving the accuracy of detecting leakage.

In the aforementioned leakage check system, each of tubular batteries Ba arranged in a predetermined manner is held on the main transfer disk 20 to be fed in a rotary scheme toward the fluorescent X-ray detection portion 13. Each of the tubular batteries Ba can be thus positively held so as not to be displaced out of position while being fed at a high speed, thereby ensuring that the sealed end face 33 of the tubular batteries Ba opposes and passes by the detection window 35 at the shortest possible constant distance D therebetween. This makes it possible to detect leakage with high accuracy while tubular batteries are detected at further increased speeds.

Furthermore, as explained in relation to FIG. 3, the fluorescent X-ray detection portion 13 is attached to the support mount 29 so that the detection window 35 on the housing 30 is oriented rearward for the primary X-ray 34 to be emitted rearward. This arrangement eliminates the risk of the operator being exposed to the primary X-ray 34 when working in front of the support mount 29 opposite to the attachment of each of the transfer disks 18, 20, 21, and 24, thereby providing a very safe leakage check system.

Furthermore, as shown in FIG. 5, the shape of the opening of the detection window 35 can be varied as desired by controlling the opening control member 42. Accordingly, when different tubular batteries Ba are to be checked, the opening control member 42 can be adjusted to accommodate the diameter or the outer shape of the tubular batteries Ba. This makes it possible to readily perform a leakage inspection on various types of tubular batteries Ba such as cylindrical batteries Ba1 having different diameters or prismatic batteries Ba2 having different outer shapes.

Then, those defective tubular batteries Ba that have been determined to be leaky in the leakage inspection at the leakage check mechanism 12 are pushed out with the ejection cylinder 23 (see FIG. 1) and thereby transferred to the ejection transfer disk 24. Here, the ejection cylinder 23 is driven at a point in time at which a tubular battery Ba is fed to oppose the ejection transfer disk 24 as the main transfer disk 20 rotates. Thereafter, the tubular batteries Ba are automatically collected such as in a bin via the ejection conveyor 27 that constitutes a defectives collection path. Accordingly, the leakage check system separates defective tubular batteries Ba from good tubular batteries Ba in a continuous transport process to automatically reject those defectives. It is thus not necessary to provide a go-or-no-go screening step that is carried out in accordance with the results of leakage inspections of tubular batteries Ba after the leakage inspection step.

Note that in the aforementioned embodiment, such an example has been illustrated in which the tubular batteries Ba are fed while being held in position on the transfer disks 18, 20, 21, and 24. However, the same effects as described above can also be obtained by allowing the tubular batteries Ba to be fed on a straight reed path while being held in position. As a matter of course, various additional components may also be employed when necessary for practical use. The detection window 35 may be provided with a shutter to block it to intercept the X-ray 34 when the system is stopped, thereby providing further enhanced safety. Furthermore, the main transfer disk 20 may be provided with an additional mechanism for rotating a held tubular battery Ba around itself only in a region where it passes by the detection window 35, thereby providing further improved accuracy of detecting leakage.

INDUSTRIAL APPLICABILITY

As described above, according to the present invention, a detection window allows an X-ray to pass therethrough and then irradiate the sealed end face of tubular batteries and allows a fluorescent X-ray emitted from the sealed end face to pass therethrough to be incident upon a fluorescent X-ray detector. The length of the detection window corresponding to the direction of feed of the tubular batteries is less than the spacing between the tubular batteries being fed. The length of the detection window in an orientation orthogonal to the direction of feed is greater than the outer size of the cross-sectional shape of the tubular batteries in an orientation orthogonal to their axial center. This makes it possible to realize a method for checking for leakage from tubular batteries, which allows for accurately determining occurrence of leakage from a tubular battery at high speeds by X-ray fluorescence analysis.

The invention claimed is:

1. A method for checking for leakage from tubular batteries, comprising:

feeding tubular batteries with respective axial centers thereof aligned in parallel to each other to pass through a leakage check section placed opposite to a detection window of a leakage check mechanism;

irradiating a sealed end face of the tubular battery in the leakage check section with an X-ray through the detection window and allowing a fluorescent X-ray coming out of the sealed end face to enter a fluorescent X-ray detector through the detection window; and analyzing whether a fluorescent X-ray associated with an electrolyte component is contained in the incident fluorescent X-ray to thereby determine whether leakage occurs from the tubular battery, wherein the detection window is defined in such a shape that a length thereof in a direction of feed of the tubular batteries is less than a spacing between the tubular batteries being fed, and a length thereof in an orientation orthogonal to the direction of feed is slightly larger than an outer size of the cross-sectional shape of the tubular batteries in an orientation orthogonal to their axial center.

2. The method for checking for leakage from tubular batteries according to claim 1, wherein occurrence of leakage is detected in accordance with an intensity per unit time of the fluorescent X-ray successively entering the fluorescent X-ray detector from each tubular battery which sequentially comes to oppose the detection window while being fed, or in accordance with an intensity per unit area of the sealed end face of the tubular battery.

3. The method for checking for leakage from tubular batteries according to claim 1, wherein: the detection window of the leakage check mechanism is disposed to oppose the sealed end face of the tubular battery being fed at a predetermined distance therebetween; a housing of the check mechanism contains an X-ray source for emitting an X-ray to a tubular battery, a mask for condensing a fluorescent X-ray emitted from the X-ray source into a beam, and the fluorescent X-ray detector upon which the fluorescent X-ray is incident; and the inside of the housing is kept in a helium gas atmosphere.

4. The method for checking for leakage from tubular batteries according to claim 1, wherein the tubular batteries are fed while being held on transfer disks in parallel to each other at regular intervals.

5. The method for checking for leakage from tubular batteries according to claim 4, wherein a housing which accommodates an X-ray source, a mask, and the fluorescent X-ray detector is installed in front of an apparatus casing, to which the transfer disks for feeding the tubular batteries are attached, so that the detection window provided on the housing opposes the transfer disks.

6. The method for checking for leakage from tubular batteries according to claim 5, wherein each of the tubular batteries is held in position on the transfer disks to pass through the leakage check mechanism so that a defective tubular battery which is determined to be leaky as a result of a check in the leakage check mechanism is rejected from the transfer disks onto a detectives collection path in order to be separated from a good-battery feed path.

7. The method for checking for leakage from tubular batteries according to claim 1, wherein an alkaline battery made up of an electrolyte containing a potassium hydroxide solution is checked to determine occurrence of leakage based on whether a fluorescent X-ray associated with a potassium component is contained in the fluorescent X-ray incident upon the fluorescent X-ray detector.

8. The method for checking for leakage from tubular batteries according to claim 3, wherein the mask formed of a metal that does not transmit an X-ray is allowed to condense an X-ray emitted from the X-ray source into a beam, and the beam is then transmitted through the detection window on the housing to the sealed end face of the tubular batteries being fed, and wherein at least a length of the detection window in the direction of feed of the tubular batteries is made variable.

* * * * *